(12) United States Patent
Stach

(10) Patent No.: US 8,242,317 B2
(45) Date of Patent: Aug. 14, 2012

(54) METHOD FOR RECOVERY OF HALOGENATED HYDROCARBONS

(75) Inventor: Helmut Stach, Prieros (DE)

(73) Assignee: ZeoSys GmbH, Berlin (DE)

(*) Notice: Subject to any disclaimer, the term of this patent is extended or adjusted under 35 U.S.C. 154(b) by 0 days.

(21) Appl. No.: 12/830,065

(22) Filed: Jul. 2, 2010

(65) Prior Publication Data

US 2010/0331584 A1    Dec. 30, 2010

Related U.S. Application Data

(63) Continuation of application No. PCT/EP2008/050019, filed on Jan. 2, 2008.

(51) Int. Cl.
*C07C 17/38* (2006.01)

(52) U.S. Cl. ..................................................... 570/262

(58) Field of Classification Search .................. None
See application file for complete search history.

(56) References Cited

U.S. PATENT DOCUMENTS 6,066,192 A    5/2000    Toshinaga et al.

FOREIGN PATENT DOCUMENTS

| EP | 0 284 227 | | 3/1988 |
|---|---|---|---|
| EP | 1 115 729 | A1 | 11/2001 |
| EP | 1 459 799 | A1 | 9/2004 |
| JP | 9047635 | A | 2/1997 |
| JP | 2000300955 | A | 10/2000 |

*Primary Examiner* — Sudhakar Katakam

(74) *Attorney, Agent, or Firm* — Oblon, Spivak, McClelland, Maier & Neustadt, L.L.P.

(57) ABSTRACT

Recovery of a halogenated hydrocarbon is performed by removing the halogenated hydrocarbon from an accompanying gas and/or temporarily storing the halogenated hydrocarbon on sorption filters, and releasing the halogenated hydrocarbon in targeted manner. The halogenated hydrocarbon serves for removal of an expiration gas using a steam carrier. A flow of the halogenated hydrocarbon takes place through two sorbents, (1) a hydrophobic carbon molecular sieve and (2) a hydrophobic zeolite, in two sorbent beds, spatially following one another. Air mixed with steam or steam has a temperature of the gases between 90° C. and 100° C. at normal pressure. In a filter for carrying out theabove recovery method, two filter beds are disposed to spatially follow one another.

7 Claims, 1 Drawing Sheet

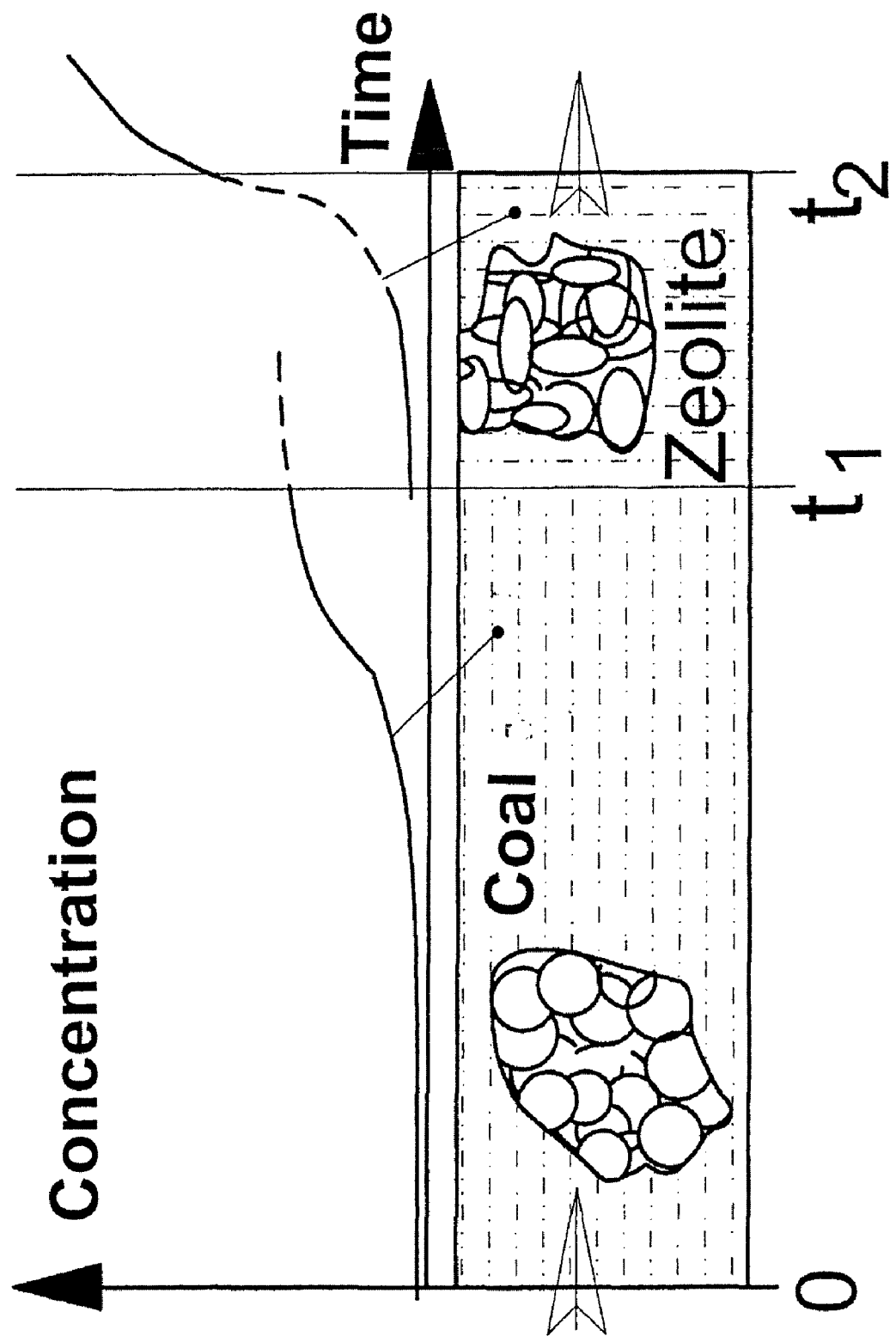

METHOD FOR RECOVERY OF HALOGENATED HYDROCARBONS

BACKGROUND OF THE INVENTION

1. Field of the Invention

The invention relates to a method for recovery of a halogenated hydrocarbon, particularly of an inhalation anesthetic, and to a filter for this purpose.

2. Description of the Related Art

Sorption processes are frequently used for separation, purification, and drying of gases. In this connection, there are requirements for exhaust air charged with halogenated hydrocarbons (HHCs) that boil at a low temperature, as dictated by ecological requirements.

Anesthetics that evaporate easily and are frequently used in medical practice, such as enflurane, isoflurane, sevoflurane, and desflurane, are hydrocarbons or ethers substituted with fluorine and chlorine, which are usually completely released into the surroundings during or after anesthesia, and can harm both patients and medical personnel. Furthermore, they contribute to the "ozone hole" or to the "greenhouse effect." An estimate regarding the member states of the EU showed that in 1995 alone, pollution of the atmosphere with approximately 700 metric tons of inhalation anesthetics occurred. This amount corresponds to an additional carbon dioxide burden on the environment of 0.25% [Zeitschr. Andsthesiologie u. Intensivmed. {Journal for Anesthesiology and Intensive-Care Medicine} 6 (39), 301-306, 1998]. Both in productive processing and in the recovery of HHCs from exhaust air, particularly from expiration air of patients that is charged with inhalation anesthetics, it is a concern to work towards an economically efficient configuration of the sorption filters and related methods.

Activated charcoals that have a reactive effect are already suitable for purification of process air or exhaust air (DE 37 13 346, DE 39 35 094, and DE 40 03 668). The prerequisites for high sorption capacity combined with optimal regenerability have already been explained in the references DD 239 947, DE 36 28 858, and DE 37 31 688. The recovery of HHCs can take place at a high degree of recovery, by means of desorption at high temperatures and low pressures. In the end result of the heat treatment, however, structural damage of the sorbents and the formation of decompositions products of the HHCs, which products contain halogens, take place.

In DE 37 13 346 and DE 195 49 271, DE 42 33 577, removal of HHCs by means of zeolites is described. Zeolites have a high thermal stability for the sorption of inhalation anesthetics, and a low catalytic activity with regard to any formation of toxic products. In recent times, zeolites that are low in aluminum or de-aluminized have been used as sorption agents (DE 195 32 500).

It is known that after separation and recovery of inhalation anesthetics on activated charcoal filters or zeolite filters, other accompanying gases were simply combusted (DE 42 08 521). In this way, active substances that can be recovered are irreversibly withdrawn from the filters. In contrast, HHCs are permanently absorbed in activated charcoals having a broad pore spectrum, in the narrow pores. In the recovery of inhalation anesthetics (DE 43 08 940 and DE 195 49 271), high desorption temperatures lead to by-products that have a medically questionable effect.

Hydrophobic zeolite molecular sieves having a narrow pore distribution are used for recovery of HHCs (EP 0 284 227). Desorption takes place below 150° C. The inhalation anesthetics are condensed out and recovered. In this connection, decomposition products cannot yet be excluded.

De-aluminized zeolites adapted to the methods have already been advantageously used as sorbents (DE 197 49 963). The sorbed HHCs are desorbed by means of heating, condensed, and recovered. Because of high vapor pressures of the anesthetics, condensation must take place in a range of 2° C. to 8° C. The desorption of isoflurane takes place under vacuum (approximately 10 mbar), and with simultaneous heating to about 100° C. to 160° C. The maximal desorption temperature therefore lies about 60° C. lower than for activated charcoal. Desflurane is desorbed between 90° C. and 130° C.

Regeneration that is gentle on the cartridge, with a steam carrier, is described in DE 101 18 768. Modified and/or de-aluminized zeolites having low water absorption below ma-2% bring about a lowering in the desorption temperature that is gentle on the sorbent and on the sorbate. It is advantageous if a saturated steam temperature under normal pressure of about 100° C. is adjusted. The condensation of the gases leads to the formation of a liquid mixture that is pre-separated in layer-like manner. The specifically lighter water layer is recirculated back into the evaporation process, while the heavier layer of the inhalation anesthetics is subsequently purified. However, possible decomposition products accumulate in the water layer.

Conventional filter arrangements have different characteristics with regard to adsorption and desorption of inhalation anesthetics, in terms of their parameters, and these are significantly dependent on the conditions for flow and temperature. In order to achieve uniformity of the process management without any time delay (hysteresis), a different energy feed is provided for a filter cartridge, for example, whereby the adsorbed anesthetics can be released again from the interior of the cartridge, in targeted manner (EP 0 611 174, EP 1 222 940). Sorbents that have different effects are not yet used in combination. Also, specially shaped configurations of filter inserts for respiration gases are usual, in order to use up the contents uniformly, even at higher flow speeds (DE 36 12 924) and to prevent local break-throughs through the filter layer.

In a proposal by the applicant, "Filterpatrone zur Rückgewinnung niedrigsiedender halogenierter Kohlenwasserstoffe {Filter cartridge for recovery of halogenated hydrocarbons that boil at low temperatures}," the gas pass-through in the upper wall region of a single filter insert is configured in such a manner that a plug flow for the gases occurs in this region, thereby achieving uniformity of the break-through curves for inhalation anesthetics. The anesthesia gases used therefore have "good" break-through curves at the upper edge of the filter insert having the hydrophobic zeolites, in other words with a very steep characteristic of the transition, which is clearly determined in terms of both location and time, in that a sharp boundary forms between the charged and not yet charged parts of the zeolite fill.

The filter system, which is complex in its effect, is difficult to understand clearly and permits a possible determination of best values for its time sequence only on the basis of long-term and empirical work experience that has been gained. In particular, placement in multiple sorbent beds is problematical, where filters that can be handled in medical technology, in particular, are supposed to demonstrate a steep characteristic of the break-through curve, with times that can be precisely determined.

Multi-Stage Filter Arrangements

There has been no lack of attempts to increase the degree of charging of sorption beds during targeted purification of gas streams. In DE 43 19 327, an untreated gas stream is passed through two sorption beds, one after the other. After the process has been completed, the first sorbent bed is regenerated and the flow direction is reversed, so that the flow passes through the second bed first. However, in this connection, the used sorbent is replaced with freshly regenerated sorbent, in complicated manner.

According to DE 198 26 684, a gas mixture is brought into contact with a sorbent at higher pressure, whereby a component of the mixture sorbs preferentially in a first work stage, and is desorbed in a second work stage, under reduced pressure. The two regions are separated from one another in such a manner that only the sorbed component passes over into the second region. Rectification of gas components that boil at low temperature is combined with alternating-pressure adsorption. The mechanical device for this has a complicated structure and does not meet the requirements for simple filter arrangements.

It is also state of the art that an improvement in sorptive separation is made possible by means of physical differences, for example in the pore sizes and by means of changes in the sorbent beds themselves. In the case of gas components that are not the same, like the ones that form the mixture components of laughing gas and anesthetic vapors in DE 197 06 806, their selective separation can take place by means of different types of molecular sieves. These can be used mixed with one another, or can be placed in two sorbent beds that are different from one another. In this connection, they have different pore sizes, which also could lead to sequences of the sorption processes that are different in terms of time. Two molecular sieve regions are provided, each having different ranges of pore sizes, of 0.8-1 nm and 0.3-0.5 nm, and flow takes place through them one after the other, in terms of space. While good adsorption properties are claimed for both gases, these are made possible on the basis of purely steric and thus static influences in the adjustment of the sorption equilibria. Recover by means of a carrier gas or carrier vapor is not yet taken into consideration. In particular, it is not taken into consideration that when sorption capacities that are higher than those present with zeolite molecular sieves, such as in the case of carbon molecular sieves, special dynamic influences occur, which additionally improve the sorption properties as well as the recovery of the anesthetics by means of regeneration using steam.

Process Management of HHC Filters:

In previous filter arrangements, the process management is essentially controlled, to some extent, by means of conditions that can be established macroscopically, and according to geometry parameters and operating parameters. In contrast, the separation precision of substance separation by means of sorption is necessarily determined by microscopic parameters. Differences in the molecule size in the spatial lattice structure of the sorbents bring about static sieve effects and blockages when passing through the lattice. In contrast to this, the time progression of the separation processes in the related filters is established by means of kinetics that have a complicated and dynamic effect, with marked non-idealities.

Improvements in sorptive substance separation can be provided by means of changes in the process management. In a monograph, "Adsorptionsverfahren zur Wasserreinigung {Adsorption Methods for Water Purification}" by Sontheimer, Frick, Fettig, Horner, Hubele, and Zimmer, DVWG-Forschungsstelle {test laboratory} at the Engler-Bunte Institut {institute} of the Technical University of Karlsruhe, Karlsruhe 1985, methods of procedure that have at least two stages, with flow in the same direction, for sorption beds disposed one behind the other, are proposed; their calculations lead to the best possible values of the end concentration after the first or additional sorption bed, and allow an advantageous distribution of the masses of similar types of sorbents on multiple sorption beds at a predetermined total mass. These recognitions are based on adjusted sorption equilibria and can be transferred to filter arrangements for HHCs. In particular, it has become known that carbon molecular sieves that are suitable for the sorption of inhalation anesthetics often demonstrate a greater charge than zeolites. However, in contrast to zeolites, carbon molecular sieves tend to have a disadvantageous break-through behavior, with insufficient utilization of the capacity of the filters. It is disadvantageous that the desorption curves of activated charcoals run flatter, while it is advantageous that their sorption capacity is greater.

Zeolites already possess high charge values for halogenated hydrocarbons. However, activated charcoals demonstrate a higher substance throughput at lower desorption temperatures, and thus can purify the exhaust air better.

In the determination of break-through times in filter arrangements from break-through curves, it turns out that in the event of desorption of a filter with a zeolite, shorter times to break-through are set, with a steep progression of the curves. In contrast, longer break-through times are observed when using carbon molecular sieves, with a flat progression of the break-through curves. The individual static and dynamic influence variables are difficult to separate from one another in the case of filters for HHCs and inhalation anesthetics, and therefore can hardly be investigated independent of one another. For this reason, it is difficult to make use of the individual advantages of the use of sorbents that have different effects, without optimization. For this reason, it is an urgent concern to establish the set-up of at least two sorbent beds of a filter arrangement that work together as practically as possible.

It has not yet been found that a combination of hydrophobic zeolites with activated charcoals is practical for determining the best values of proportions in at least two sorption beds of filters for inhalation anesthetics.

SUMMARY OF THE INVENTION

It was an object of the present invention to develop a method in which the disadvantages described in the background art can be eliminated.

This and other objects have been achieved by the present invention the first embodiment of which includes a method for recovery of a halogenated hydrocarbon, comprising:

removing said halogenated hydrocarbon from an accompanying gas; and/or temporarily storing said halogenated hydrocarbon on sorption filters, and releasing said halogenated hydrocarbon in targeted manner, and wherein said halogenated hydrocarbon primarily serves for removal of an expiration gas using a steam carrier, wherein flow of said halogenated hydrocarbon takes place through two sorbents, (1) a hydrophobic carbon molecular sieve and (2) a hydrophobic zeolite, in two sorbent beds, spatially following one another, wherein (i) air mixed with steam or (ii) steam has a temperature of the gases between 90° C. and 100° C. at normal pressure.

In another embodiment the present invention relates to a filter for performing the above method.

BRIEF DESCRIPTION OF THE DRAWING

The FIGURE shows a filter arrangement with two sorption beds and characteristic break-through curves.

DETAILED DESCRIPTION OF THE PREFERRED EMBODIMENTS

All ranges described below are understood to explicitly include all subvalues between the lower and the upper limit.

In one embodiment, the invention relates to a method and a filter for recovering low-boiling halogenated hydrocarbons (HHC), in particular for inhalation anesthetics such as desflurane, enflurane, isoflurane and sevoflurane. The method allows effective charging by adsorption and also effective regenerating via desorption by means of steam on two successive sorption beds which comprise hydrophobic molecular graded coal and hydrophobic zeolite.

According to the invention, a method was provided in which spatially separated sorption of substance amounts that can be sorbed in different ways is established for a two-stage filter arrangement, by means of time influences.

With this, the result is achieved that a first sorption bed having a hydrophobic carbon molecular sieve is placed ahead of a second sorption bed having a hydrophobic zeolite, in series (one behind the other). The two each represent a process stage and the sorptive flows through them one after the other, in terms of space. The two states have a common throughput parameter for the carrier gas, particularly for air, but also, during regeneration, for the regeneration agent, steam. These process variables are, of course, dependent on the gas pressure and on the temperature, as well as on the amount of gas in the stream of the carrier gas. The filter arrangement can act continuously in a production system or gas purification system, or can also be configured as a filter cartridge that can be regenerated or, for practical purposes, evacuated. Sorption from the carrier gas, particularly desorption into the carrier gas and distillation with saturated steam are combined with one another. In this connection, the temperatures are lowered for regeneration, to as low as 10° C., under normal pressure, and the sorbents as well as the sorbates are handled gently, in thermal terms. It is possible to additionally lower the temperatures for the regeneration by lowering the pressure by means of applying a vacuum. The velocities of the expiration gases as they flow through the consecutive stages amount to 0.2-0.3 m/s, the steam speeds with reference to the flow cross-section during regeneration amount to as much as 0.4 m³/(m² h), without the break-through curves being deformed to a noteworthy extent. The disadvantageous break-through curve of the carbon filter bed is transformed to an advantageous one by means of the additional zeolite bed in the filter arrangement.

Zeolites having an internal surface area of preferably 800-1000 m²/g and having an average pore diameter of approximately 0.8 nm are used. The use of de-aluminized zeolites and those of the faujasite type is particularly advantageous. Substances having internal surface areas of preferably 1000-1400 m²/g and having an average pore diameter of 0.5 to 1 nm are possible as carbon molecular sieves.

The invention will be explained using examples and two tables, without the invention being restricted to these examples. The FIGURE shows filter arrangement with two sorption beds and characteristic break-through curves and, related to that is the following optimization procedure:

Optimization $$m_T = m_1 + m_2 = \frac{V_1}{q_1}\int_0^\infty [c_0 - c_1(t)]\,dt + \frac{V_2}{q_2}\int_0^\infty [c_1(t) - c_2(t)]\,dt$$

$$\frac{dm_T}{dc_1} = 0 \ldots \Rightarrow \frac{q_1}{q_2} = \frac{t_2 - t_1}{t_1}\left[1 + n_1\int_0^\infty\left(\frac{c_0}{c_1(t)} - 1\right)dt\right]$$

$$\ldots \Rightarrow \frac{m_1}{m_2} = \frac{t_1}{t_2 - t_1}\frac{q_2}{q_1}\int_0^\infty\left(\frac{c_0}{c_1(t)} - 1\right)dt$$

$$\text{at } c_2 \to 0;\ q_i = K_i c_i^{n_i};\ t_i = \frac{V_i}{\dot V}\ i = 1, 2$$

Having generally described this invention, a further understanding can be obtained by reference to certain specific examples which are provided herein for purposes of illustration only, and are not intended to be limiting unless otherwise specified.

EXEMPLARY EMBODIMENTS

Reference Symbol List c concentration
DBK break-through curve
K constant (Freundlich isotherms)
m mass
MTZ mass transition zone
n exponent (Freundlich isotherms)
q charge
t time
V volume
$\dot V$ volume stream
w velocity, with reference to cross-section
Z bed height
Indices
B with reference to sorbent bed
i number of stages
max largest possible
T total; entire
0 stage entry
1 1$^{st}$ stage
2 2$^{nd}$ stage Example 1

An inhalation anesthetic flowed through a combined filter, under mild conditions of 20° C.-30° C., and under normal pressure, which filter had an activated charcoal bed and a bed comprising a zeolite. The flow velocities with reference to the cross-section of the filter beds were set at approximately 0.05 m/s, according to Table 1, in such a manner that sorption equilibrium almost existed within the two stages, between the sorbents and the anesthetic.

TABLE 1

Optimized parameters of a two-stage sorption

| Parameter | Step No. | Value | Dimension |
|---|---|---|---|
| Input concentration | 1 | 5.0 | mol · l⁻¹ |
|  | 2 | 1.2 |  |
| Output concentration | 1 | 1.2 | mol · l⁻¹ |
|  | 2 | 0.05 |  |
| Corrected bed volumes | 1 | 1.5 | l |
|  | 2 | 0.5 |  |
| Constants of the Freundlich isotherms | 1 | 3.0 | mol$^{1-n}$ · l$^n$ · kg⁻¹ |
|  | 2 | 2.0 |  |
| Exponents of the Freundlich isotherms | 1 | 0.5 | — |
|  | 2 | 0.2 |  |
| Charge of the I sorbents | 1 | 3.3 | kg/kg |
|  | 2 | 1.9 | sorbent |
| Amounts of the sorbents | 1 | 1.7 | kg |
|  | 2 | 0.3 |  |

Example 2

In each instance, 50 g sorbent were provided and sevoflurane flowed through them, contained at 1.5% in air at 28° C. According to Table 2, the following were determined for carbon molecular sieves and zeolites:

maximal charges $q_{max}$;
average break-through times $t_B$ on the basis of 5% of the break-through start and 95% of the break-through end,
average half-value widths $\Delta t_B$, in terms of time, for the break-through times,
relative half-value widths $\Delta t_B/t_B$, in terms of time, related to this,
the mass transition zone MTZ=$2 \cdot w_B \cdot \Delta t_B$, with reference to the bed lengths Z, at which the velocities $w_B$ with reference to the flow cross-section were $w_B$=0.2 m/s,
and the quantitative progression of the break-through curves.

TABLE 2

Progressions of break-through curves on carbon molecular sieves and zeolites

| Sorbent | Type | $q_{max}$, kg/kg | $t_B$, min | $\Delta t_B$, min | $\Delta t_B/t_B$, -- | MTZ/Z, -- | DBK progression |
|---|---|---|---|---|---|---|---|
| Carbon molecular sieves | Type 1 | 0.35 | 120 | 22 | 0.18 | 7.2 | flat |
| | Type 2 | 0.78 | 270 | 45 | 0.17 | 2.4 | moderately flat |
| Zeolites | Z-700, fine | 0.21 | 62 | 5 | 0.08 | 1.2 | steep |
| | Z-700 | 0.26 | 74 | 8 | 0.11 | 1.8 | steep |
| | TZF | 0.26 | 91 | 12 | 0.13 | 2.0 | steep |

The carbon molecular sieves possess advantages because of their capacity, while the zeolites possess advantages because of their steeper break-through curves.

International patent application PCT/EP2008/050019 filed Jan. 2, 2008, is incorporated herein by reference. Priority is claimed to this application.

Numerous modifications and variations on the present invention are possible in light of the above teachings. It is therefore to be understood that within the scope of the appended claims, the invention may be practiced otherwise than as specifically described herein.

The invention claimed is:

1. A method for recovery of a halogenated hydrocarbon, comprising:
   removing said halogenated hydrocarbon from an accompanying gas; and/or temporarily storing said halogenated hydrocarbon on sorption filters, and releasing said halogenated hydrocarbon in targeted manner, and
      wherein said halogenated hydrocarbon primarily removes an expiration gas using a steam carrier,
   wherein flow of said halogenated hydrocarbon takes place through two sorbents, (1) a hydrophobic carbon molecular sieve and (2) a hydrophobic zeolite, in two sorbent beds, spatially following one another,
   wherein (i) air mixed with steam or (ii) steam have a temperature of the gases between 90° C. and 100° C. at normal pressure.

2. The method according to claim 1, wherein the carbon molecular sieve has an internal surface area of 1000-1400 m²/g, and
   an average pore diameter of 0.5 to 1 nm.

3. The method according to claim 1, wherein the zeolite has an internal surface area of 800-1000 m²/g, and
   an average pore diameter of about 0.6 to 0.8 nm.

4. The method according to claim 3, wherein the zeolite is of the faujasite type and has a water absorption capacity of less than 2 wt-%.

5. The method according to claim 1, wherein a temperature for regeneration of the sorbents are lowered by lowering the pressure.

6. The method according to claim 1, wherein a velocitiy of the expiration gas is 0.2-0.3 m/s, and a steam velocity during regeneration, with reference to the flow cross-section, is up to 0.4 m³/(m²h).

7. The method according to claim 1, wherein the halogenated hydrocarbon is an inhalation anesthetic.

* * * * *